(12) United States Patent
Metropoulos

(10) Patent No.: US 10,480,875 B2
(45) Date of Patent: Nov. 19, 2019

(54) METHOD AND SYSTEM FOR CLEANING HEATING, VENTILATION AND AIR CONDITIONING SYSTEMS

(71) Applicant: Blue Box Air, LLC, Las Vegas, NV (US)

(72) Inventor: James Metropoulos, Manhattan Beach, CA (US)

(73) Assignee: BLUE BOX AIR, LLC, Gardena, CA (US)

( * ) Notice: Subject to any disclaimer, the term of this patent is extended or adjusted under 35 U.S.C. 154(b) by 81 days.

(21) Appl. No.: 15/280,693

(22) Filed: Sep. 29, 2016

(65) Prior Publication Data

US 2017/0191768 A1    Jul. 6, 2017

Related U.S. Application Data

(60) Provisional application No. 62/234,405, filed on Sep. 29, 2015.

(51) Int. Cl.
| | |
|---|---|
| *F28G 9/00* | (2006.01) |
| *F28G 1/16* | (2006.01) |
| *A61L 2/16* | (2006.01) |
| *A61L 2/18* | (2006.01) |
| *B08B 3/00* | (2006.01) |
| *C11D 11/00* | (2006.01) |
| *C11D 17/00* | (2006.01) |

(52) U.S. Cl.
CPC .............. *F28G 9/00* (2013.01); *A61L 2/16* (2013.01); *A61L 2/186* (2013.01); *B08B 3/003* (2013.01); *C11D 11/0023* (2013.01); *C11D 11/0041* (2013.01); *C11D 11/0058* (2013.01); *C11D 17/0043* (2013.01); *F28G 1/166* (2013.01); *A61L 2202/15* (2013.01); *A61L 2202/16* (2013.01); *A61L 2202/17* (2013.01); *F24F 2221/225* (2013.01)

(58) Field of Classification Search
None
See application file for complete search history.

(56) References Cited

U.S. PATENT DOCUMENTS

| | | | |
|---|---|---|---|
| 4,332,292 A * | 6/1982 | Garberick | F28G 1/16 134/172 |
| 5,509,972 A | 4/1996 | Akazawa et al. | |
| 6,027,572 A | 2/2000 | Labib et al. | |
| 6,047,714 A * | 4/2000 | Akazawa | B08B 9/043 134/22.12 |
| 6,276,459 B1 | 8/2001 | Herrick et al. | |

(Continued)

FOREIGN PATENT DOCUMENTS

WO    WO2002094973    11/2002

OTHER PUBLICATIONS

International Search Report cited in PCT Application No. PCT/US2016/054515 dated Dec. 2, 2016.

*Primary Examiner* — Eric W Golightly
*Assistant Examiner* — Arlyn I Rivera-Cordero
(74) *Attorney, Agent, or Firm* — Workman Nydegger

(57) ABSTRACT

A method for cleaning, sanitizing, and disinfecting commercial and residential HVAC system includes applying cleaning foam to coils of the HVAC system, the foam including one or more agents that break down organic and/or inorganic fouling debris into particles, the foam removing and carrying away debris from the coils.

18 Claims, 5 Drawing Sheets

(56) References Cited

U.S. PATENT DOCUMENTS

| | | | |
|---|---|---|---|
| 7,132,017 B2* | 11/2006 | Laurence | B08B 3/02 134/30 |
| 7,841,351 B1 | 11/2010 | Kane et al. | |
| 7,887,639 B1 | 2/2011 | Ratliff et al. | |
| 9,676,007 B1* | 6/2017 | Kane | B08B 3/026 |
| 2008/0193650 A1* | 8/2008 | Lyon | A01N 59/00 427/299 |
| 2010/0078007 A1* | 4/2010 | Post | F04D 29/422 126/112 |
| 2015/0144303 A1* | 5/2015 | Burfeind | F28G 1/166 165/95 |

* cited by examiner

METHOD AND SYSTEM FOR CLEANING HEATING, VENTILATION AND AIR CONDITIONING SYSTEMS

CROSS-REFERENCE TO RELATED APPLICATIONS

This application claims the benefit of U.S. Provisional Patent Application No. 62/234,405, filed Sep. 29, 2016, the disclosure of which is incorporated herein in its entirety.

BACKGROUND OF THE INVENTION

1. The Field of the Invention

The invention relates to methods and systems for cleaning and sanitizing heating, ventilation, and air conditioning (HVAC) systems, including heat transfer coils.

2. The Relevant Technology

HVAC systems typically consume over 50% of a building's total energy. It is estimated that roughly half of this energy is wasted because the heat transfer coils in HVAC systems are operating in a fouled condition. Such fouled coils are the primary source of many operational problems found within HVAC systems, such as excessive equipment wear and tear, decreased human health due to poor indoor air quality, and excessive energy consumption. Hydrocarbon buildup from outside air pollution, pollen, dust, and grease are examples of common materials causing coil fouling.

Another common form of fouling arises from the formation of bacteria and fungi deep inside the coils. This biological form of fouling is exceptionally problematic for HVAC systems. When microbes take root deep inside the coils they begin to form biofilms, which is a plasticity type of membrane excreted by these micro-organisms. Biofilms are particularly detrimental to the HVAC system because these films are highly conductive which works to inhibit heat transfer between the metal surfaces of the coil and the passing air flow. In addition, biofilms can have sticky surfaces that can accumulate dust and the other fouling debris, thereby acting to inhibit air flow and efficient heat transfer though the coils.

When bacteria and fungi take root deep inside HVAC coils, many other operational problems can arise outside of inhibited air flow and heat transfer. As colonies of these microbes grow, their biological activity begins to off-gas noxious odors, creating a common problem in HVAC referred to as "Dirty Socks Syndrome"—a condition where the air supply in a building begins to present with a foul smell of dirty socks or other types of unpleasant smell.

For hospitals, biological fouling of HVAC coils is especially problematic and can present a near epidemic level problem for the global health care system. In the last several years, hospitals have seen a frightening rise of antibiotic resistant bacteria, such as Staph, MRSA, and others, taking root within nearly all medical facilities. It is now becoming a relatively common occurrence for sick patients to come into a medical facility needing treatment for one condition and then becoming infected with an antibiotic resistant strain of another illness contracted while visiting the hospital. In spite of extensive and vigilant sanitizing and cleaning efforts, medical facilities have so far been unable to eliminate dangerous microbes from the medical facility's operating environment. A major reason for this inability to eradicate dangerous microbes is due to the ability of antibiotic resistant microbes to hide, thrive, and migrate through the medical facility via its HVAC system. Specifically, it is deep inside the coils where antibiotic resistant microbes have found safe refuge, and the HVAC system provides means for traveling throughout the medical facility.

Cooling coils of HVAC systems within large medical facilities can range in depth from 6" to 4 feet. Spacing between fins in the coils is extremely compact, with space measured in millimeters between each fin. The objective of the coils is to provide as much surface area as possible within a confined space, making the space between fins only large enough to permit air to pass through. In addition, the cooling coils in large facilities can often reach 15 feet in height and are sealed on top so that air can flow evenly through the coils. This means there is often no way to access coils from the sides or the tops of the system. The density of the packed coils serves to inhibit liquids from traveling more than 2 inches inside the coils, which leaves the vast majority of internal coil surface area completely inaccessible for cleaning.

The result is that internal surface area of HVAC cooling coils provide an ideal sanctuary for antibiotic resistant, and all other bacteria and fungi, to take root and thrive within a medical or other facility. Because the objective of the HVAC system is to circulate air throughout the facility, dangerous microbes can be carried in the air stream and efficiently spread throughout the facility. While a medical facility can be extremely vigilant in cleaning all exposed surface areas throughout the facility, the inability to sanitize and disinfect deep inside the coils leaves these facilities exposed and unable to fully mitigate dangerous risks posed by traveling microbes.

The standard practice employed throughout the HVAC industry, hotels, hospitals and other facilities is to clean HVAC coils using pressure washers. Another practice is to inject highly caustic or acidic solutions into the coils via a pressure washer or a hand held pump spray device. Yet another practice is to inject steam into the coils. These practices are completely ineffective in penetrating completely through the coils, especially coils deeper than 6 inches. These processes are also ineffective in removing biofilms or in sanitizing and disinfecting deep internal surface areas of the coils. In addition, all of these processes require complete shutdown of the air handler in order to service and are often damaging, wasteful, and hazardous to the environment.

Pressure washing, by far the most commonly employed practice in cleaning HVAC coils, involves the use of high pressure water, often exceeding 1,000 psi, to create a pressurized stream of water which is applied to the coil's outer surfaces. However, the dense packing of the coils acts to prevent water from penetrating more than about 2 inches into the coils, regardless of the injection of high pressure water. The tightly packed coils absorb the energy and deflect the pressurized water stream. In addition, due to weight of water and force of gravity, when the pressurized water stream loses kinetic energy due to absorption by the coils, the water naturally falls vertically towards the ground. Another weakness of pressure washing is that at 1,000+ psi the force of the pressurized water stream can quickly and easily bend the coil fins. The coils themselves are tightly packed and made from very thin soft metals, such as aluminum or copper. Once coils are bent and damaged in this manner, air flow is further restricted and made uneven, further reducing flow-through efficiency of the air handler. In addition, pressure washers utilize enormous quantities of water. Pressure washers can consume from 6-20 gallons per minute depending on their size. At the smallest version of 6 gallons per minute, a 1-hour cleaning of coils can result in the consumption of 360 gallons of water. It is not uncommon to consume well over 1,000 gallons of water during the cleaning of one large air handler.

Another technique for cleaning coils involves the use of a handle held pump spray and the direct injection of a caustic or acidic coil cleaner. This process is typically performed at lower pressure compared to high pressure washers. The idea behind caustic coils cleaners is to remove biofilm buildup inside the coils. Unfortunately, biofilms can present a plasticity type of membrane that is impervious to caustic, acidic, and even oxidizing solutions. In addition, caustic solutions can actively react with and strip layers of metal molecules from the coil surfaces. This is highly damaging and often leads to complete destruction of the coils over relatively short periods of service time. Finally, the pump spray method of injecting a caustic solution into coils experiences the same physical issues of pressure washing where only the surface and perhaps a few inches in depth are actually penetrated.

Another technique used to clean coils involves injecting the coils with high temperature steam. In this process, high temperature steam is directly injected into the coils with the hopes that the steam will physically break down biofilm, bacteria, dirt and grime. However, steam injection faces similar physical barriers as pressure washing because the outer coil surfaces can absorb kinetic and heat energy of the injected steam and inhibit its penetration to only a few inches. In addition, while steam may kill some of the bacteria and fungi near the outer coil surfaces, high temperatures are typically ineffective in removing the actual biofilm layer. In addition, the use of high temperature steam in many physical locations within a facility is impractical and can set up fire systems due to its excessive heat.

The ability to clean and sanitize cooling coils found in HVAC systems without damaging or shutting down the HVAC system is a solution that provides a whole new approach to significantly reduce energy consumption, reduce $CO_2$ output, and greatly improve human health. To date, this process has been shown to improve the efficiency of commercial air handlers by up to 80%, which has been achieved by removing the fouling debris build up deep inside the coils. The HVAC system is also able to then greatly improve the volume of air moving through the air handler with less energy load. In addition, the innovation that will be outlined below is a scalable solution that is easy to apply and adopt, eliminates the need to invest in costly new capital equipment, and delivers its beneficial results immediately. This innovation is also a single platform solution that can be applied to any size or type of HVAC system and is equally effective if the HVAC system is a push or a pull type system. This means the blower within the air handler is pushing air through the coils or drawing air, via a reverse suction, of air flow. In addition, the described invention provides a means to deliver near perfect surface area coverage deep within the cooling coils that makes it possible to remove all biofilms, as well as eliminate any bacteria, fungi and other microorganisms that are found deep within HVAC coils and provide a highly effective and cost effective solution for medical facilities to quickly and effectively mitigate their antibiotic resistant microbe crisis by sanitizing and disinfecting the sole area within the medical facility (deep inside the coils) that is currently unreachable. Finally, this innovation is a truly sustainable solution. The process that will be described below uses roughly 95% less water than conventional methods of pressure washing, and no toxic, hazardous, or damaging chemicals. In addition, this solution is low pressure, making it impossible for the described process to deliver any damage to the HVAC coils.

SUMMARY

Disclosed herein are apparatus and methods for efficiently cleaning heat transfer coils of HVAC systems, which delays or eliminates the need to replace the coils and/or improves energy efficiency and air quality of industrial, commercial and residential HVAC systems. The apparatus and methods facilitate sanitizing and disinfecting coils of bacteria, fungi, and viruses, and make it possible to remove dirt, grime, grease or other fouling debris that may collect deep inside the coils and fins of an air handler system. The described process can be low pressure, pH neutral, non-corrosive, non-odorous, uses very little water, and does not require shutting down the HVAC system when cleaning.

In some embodiments, a method for cleaning a heating, ventilation and air conditioning (HVAC) system of a building comprises: (1) applying a cleaning foam into a plurality of spaces between or within one or more heat-transfer coils of the HVAC system; (2) causing or allowing the cleaning foam to pass through the plurality of spaces; (3) the cleaning foam breaking down and removing debris from surfaces adjacent to the plurality of spaces; and (4) the cleaning foam carrying away the removed debris from the plurality of spaces. In some embodiments, the method further includes operating an air handler of the HVAC system, the air handler causing forced air to pass through the plurality of spaces between or within one or more heat-transfer coils, the forced air assisting movement of the cleaning foam and removed debris through the plurality of spaces.

In some embodiments, a foam generating system for producing cleaning foam used in cleaning a heating, ventilation and air conditioning (HVAC) system of a building comprises: (1) an air pump or pressurized vessel that provides pressurized air; (2) one or more inlets for receiving water, the pressurized air, and a surfactant; (3) one or more air-driven pumps for pressurizing the water and surfactant, the one or more air-driven pumps being driven by the pressurized air; (4) a manifold for receiving and mixing the pressurized air, water, and surfactant so as to form pressurized cleaning foam; and (5) an outlet in fluid communication with the manifold for discharging the pressurized cleaning foam.

DETAILED DESCRIPTION OF PREFERRED EMBODIMENTS

Figure 1:
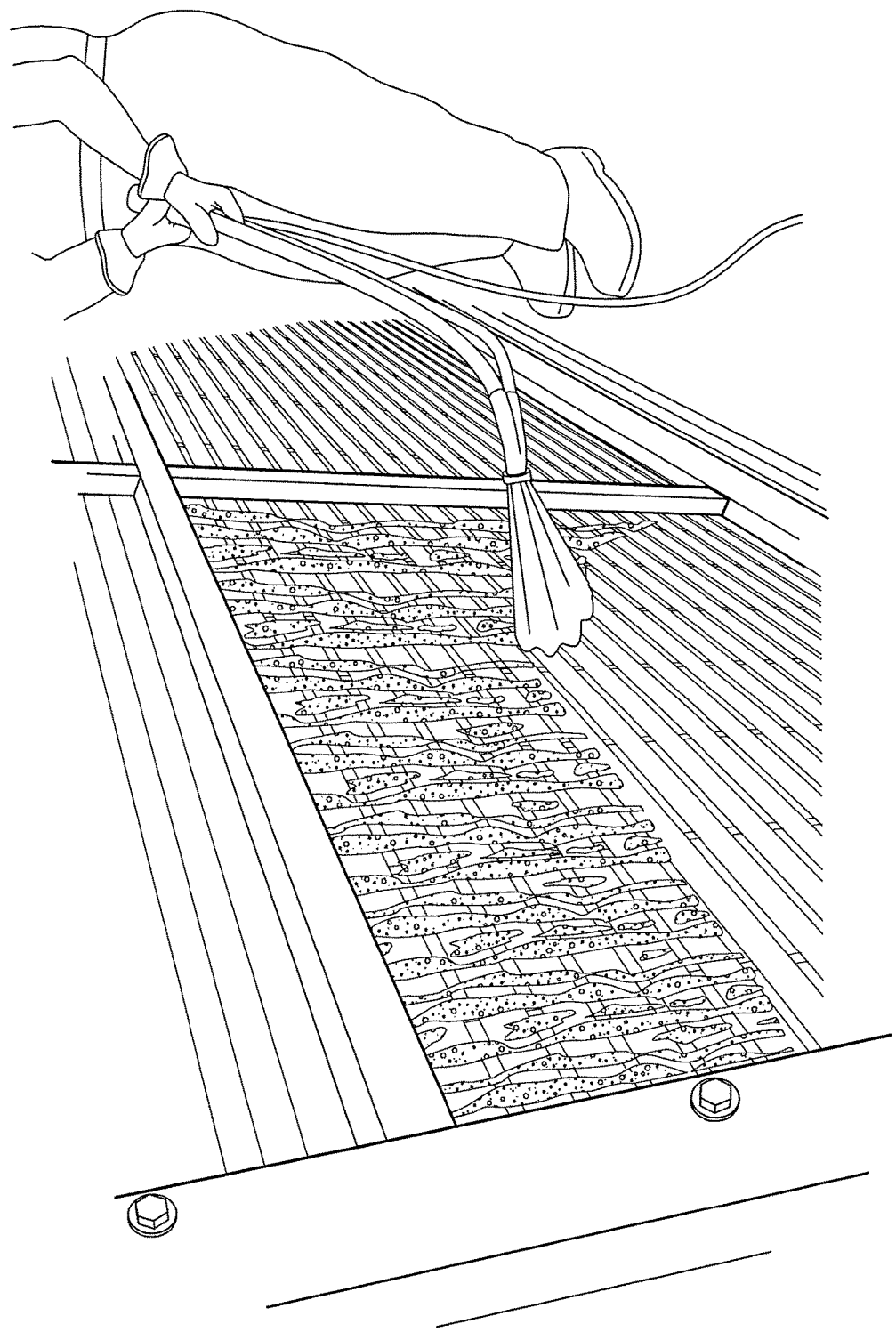
FIG. 1 depicts cleaning foam being injected into the front side of heat exchange coils of an HVAC system.

Disclosed herein is a process for cleaning heat transfer coils of an HVAC system and a system for generating cleaning foam that is compact, easy to use, and portable, that in some embodiments uses a pH neutral, non-odorous, non-toxic, non-hazardous formulation for breaking down biofilms and sanitizing and disinfecting surface areas. In some embodiments, the methods and system can employ the air handler of the HVAC system in order to assist transporting the cleaning foam through the coils, including spaces between or within the coils.

In some embodiments, a method for cleaning a heating, ventilation and air conditioning (HVAC) system of a building comprises: (1) applying a cleaning foam into a plurality of spaces between or within one or more heat-transfer coils of the HVAC system; (2) causing or allowing the cleaning foam to pass through the plurality of spaces; (3) the cleaning foam breaking down and removing debris from surfaces adjacent to the plurality of spaces; and (4) the cleaning foam carrying away the removed debris from the plurality of spaces.

In some embodiments, a method for cleaning a heating, ventilation and air conditioning (HVAC) system of a building comprises: (1) applying a cleaning foam into a plurality of spaces between or within one or more heat-transfer coils of the HVAC system; (2) operating an air handler of the HVAC system, the air handler causing forced air to pass through the plurality of spaces and assist movement of the cleaning foam through the plurality of spaces; (3) the cleaning foam breaking down and removing debris from surfaces adjacent to the plurality of spaces; and (4) the cleaning foam carrying away the removed debris from the plurality of spaces.

In some embodiments, the cleaning foam comprises water, air, surfactant, and enzymes and/or chemical(s). Water, air and surfactant generate foam when mixed. Enzymes and/or chemical(s) can break down and remove biofilms, dirt or debris adhered to or associated with the biofilm, and/or kill and remove microbes, including bacteria, viruses or fungi, and disinfect the HVAC coils. Advantageously, the cleaning foam can be free of volatile organic compounds (VOCs) and/or is pH neutral. The cleaning foam can include at least one of hydrogen peroxide, chlorine dioxide, halide salt, hypochlorite salt, organic solvent, quaternary ammonium compound, acid, base, or chelating agent.

In some embodiments, the cleaning foam can be injected under sufficiently low pressure so as to not damage the heat-transfer coils, including so as to not damage bendable heat-transfer fins of the coils.

In some embodiments, operating an air handler of the HVAC system causes forced air to pass through the plurality of spaces between or within one or more heat-transfer coils, thereby assisting movement of the cleaning foam and removable of debris through the plurality of spaces. The air handler may comprise a blower that applies air pressure to a side of the coils and pushes air through the plurality of spaces. Alternatively, the air handler may comprise a blower that reduces air pressure to a side of the coils and pulls air through the plurality of spaces.

In addition to or instead of the air handler, the method may involve introducing air from at least one of an external air supply, external fan, pressurized air line, or portable blower into the plurality of spaces to assist movement of the cleaning foam and removal of debris through the spaces of the coils.

In some cases, different types of foam can be used in sequence to address specific problems. For example, the method may involve initially applying a thicker cleaning foam to the plurality of spaces to increase residence time and contact of the cleaning foam to the surfaces and thereafter applying a thinner cleaning foam to the plurality of spaces to accelerate movement of the cleaning foam and removed debris through the plurality of spaces.

In general, removing debris from the coils causes the HVAC system to operate with reduced the energy consumption and improved air flow. In some cases the method may involve identifying one or more blockage areas within the one or more coils of the HVAC system and applying additional cleaning foam to the one or more blockage areas.

Figure 2:
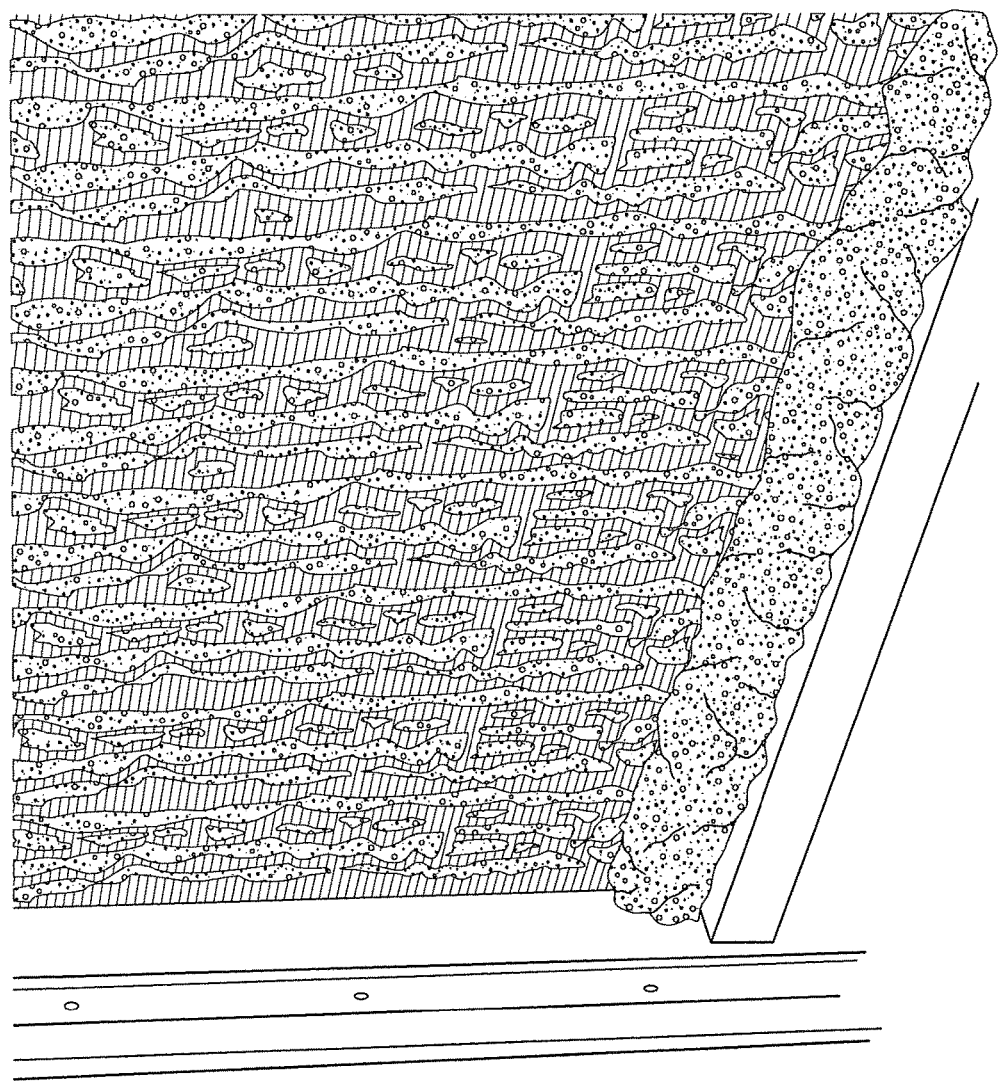
FIG. 2 depicts cleaning foam exiting the back side of the heat exchange coils of the HVAC system.
Figure 3:
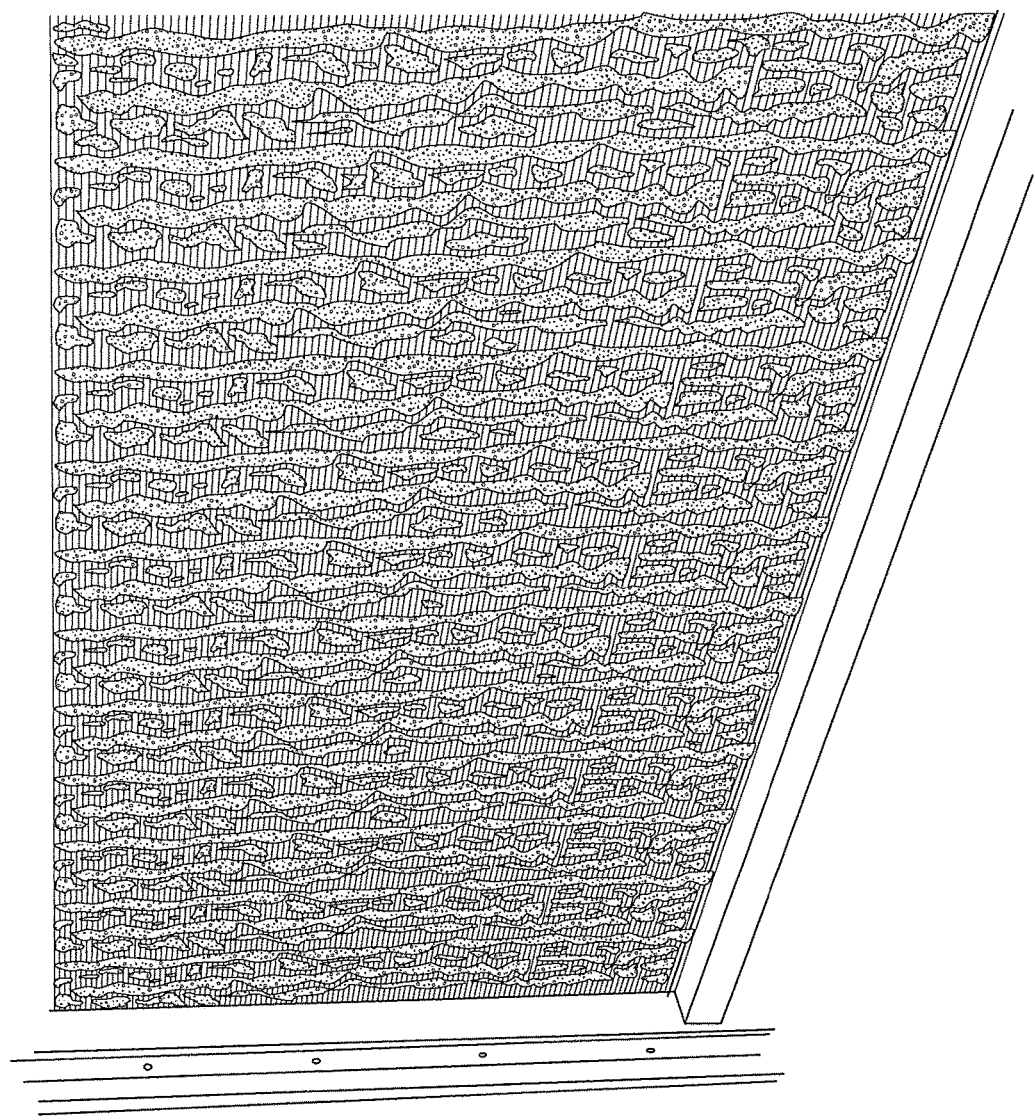
FIG. 3 depicts cleaning foam exiting the back side of the heat exchange coils of the HVAC system.

FIGS. 1-3 illustrate application of cleaning foam to one side of HVAC coils and exit of foam from the opposite side after passing through spaces within or between the coils. Preferred formulations for cleaning HVAC coils are pH neutral, non-toxic, non-hazardous, and non-odorous. In some embodiments, foam that is applied resides inside the coils and then naturally breaks down or sweats out of the system via a natural process of condensation of the coils. This helps deliver extended residence time for the activated foam to work and remove all biofilms, dirt, debris, and microorganisms.

In some embodiments the injected foam advantageously possesses no noticeable odors or changes to the smell of the air within the HVAC system. As such, the HVAC system may be cleaned without being turned off. However, changes in air quality or smells in the HVAC system is a highly sensitive situation, especially now when the prospects of potential terrorism is a real and viable concern for many people, especially those who are working in medical facilities, high rise buildings, and other public places. Conventional chemicals for cleaning coils often incorporate toxic and hazardous chemicals and generate very noticeable chemical-type odors. Even the addition of fragrances to mask these smells can cause alarms for clients because any change in air odor is readily detectable so that people quickly want to know why there is a noticeable change in air odor. For these reasons, formulations for cleaning the coils in the HVAC system can advantageously be non-odorous.

The inventive systems and methods advantageously provide more than just one way to clean coils, but rather the ability to address particular coil fouling problems with a range of cleaning solutions and techniques. This is because the fouling matrix found throughout HVAC and in the coils can vary in extremes from one environment to another. In addition, because many HVAC systems may never have been properly cleaned, they may require the removal of years, if not decades, worth of fouling. In fouling problems faced by coils, the most common problems include bacteria, fungi, and biofilms. However, coils can also be fouled with grease, hydrocarbons from outside air pollution, dust, grime, and even insect drops. It is not unusual for a cleaning process to utilize several different formulations to separately address different problems. With such an approach, a technician may be attempting to remove layers of different types of fouling issues.

For removing biofilms, there are two primary techniques. The first involves using enzymes, such as those one would find in probiotics and that actively turn the biofilm into a food source and digest the biofilm. In this approach, a wide range of enzymes can be used to address biofilms. Another approach is the use of sodium chloride which, when used in very small volumes, actively works to break down the biofilm matrix into small particles. The advantages of both approaches is that they are pH neutral, non-reactive to metal surfaces, and non-odorous. Other formulations can be introduced to help break down organics, such as traces of hydrogen peroxide or chlorine dioxide. Quaternary ammonium compounds can also be used to sanitize and kill microbes. Examples include benzalkonium chloride compounds.

In describing the presented processes, a key component to outline is how foam is injected into the coils. In this regards, the process of how foam is injected, the foam making component, and the foam composition will be described.

The technique and process of how coils are cleaned can involve harnessing the energy of the HVAC system itself as a means to either draw or push cleaning foam through the coils. As previously described above, the primary weakness of current cleaning processes involves the technical problem of how to inject cleaning solutions completely through the coils. Because of the tightly packed nature of the coils, the inability to access the middle of the coils from the top or sides, plus the natural tendency of liquids to fall by force of gravity to the bottom of the coils once they lose the pushing force of the kinetic energy to which they are being injected, means that penetrating coils more than a few of inches has typically not been possible. However, cleaning foams have properties of comprising more air than liquid and are able to cling to vertical surfaces, providing an ideal carrying mechanism for introducing cleaning solutions that can work to break down biofilms, dust, grease, and other fouling agents. In addition, cleaning foam, which comprises tiny air bubbles, possesses the unique property of being able to collect particles and keep them suspended in its bubble matrix. Analogous to how a glacier can pick up giant boulders and move them down a valley to be later deposited, foam works in a similar manner when it is flowing through a system, such as through coils of an HVAC system.

The manner in which cleaning foam is injected and migrates through densely packed, thick coils can be achieved through several techniques. First, one may simply inject a very thick foam directly into the coils where the kinetic energy of new foam will slowly push previous foam through the coils. In this technique, it may be desirable to maintain the cleaning foam as thick as possible so that it clings to metal surfaces adjacent to spaces within and through the coils, yet the density of the foam itself pushes itself through the coils. While this technique can achieve the desired results, it is a relatively slow process if the technician is using the foam injection system itself as the primary motive force of pushing foam through the coils.

Another technique involves the combination of the foam injection system and the use of one or more external air injection air supplies, such as pressurized air from air compressors or external blowers, which simultaneously are injecting air into the coils, generating an air stream that then helps push the injected foam through the coils. Again, this process is adding more volume of air through the coils, which then helps the foam migrate through the coils.

Yet another technique is to harness the HVAC system's own internal blower system to serve as the primary driving force that facilitates migration of cleaning foam through the HVAC coils. In this technique, a first technician can enter the air handler via its access door, carrying a foam spraying or injecting hose connected to a foam producing system (e.g., system 400, described below). A second technician can activate the foam producing system and, while the air handler is on and drawing in air, the first technician begins applying cleaning foam evenly over the coils. As the technician begins to apply foam onto the surface of the coils, very often it is noticed that some areas of the coils quickly draw foam in, while other areas do not. This provides a visual indication of the existence and location of blockage areas within the coils.

Blockages may include areas in the coil where the fouling is such that very little, if any, air is able to pass through due to extreme buildup of debris. Blockage areas significantly reduce the flow efficiency of HVAC coils and inhibit heat transfer. When cleaning foam quickly accumulates where the blockage areas are located, the technician can then employ several techniques to address these blockage areas. One technique is to target the foam towards the outer perimeter of the blockage area and slowly dissolve out the outer edges of the blockage area using and outside-in approach. A second approach is to inject the blockage area with a combination of very thick and very thin, or soupy foam. This technique often opens up very small air channels in the middle of the blockage areas, which then create suction holes to draw in more foam, which, through a process similar to water erosion, increases the size of the air gaps, making it possible to migrate particles and push foam through these blockage areas, thereby opening then up.

While injecting foam into the coils, the objective is to deliver near 100% surface area contact. As the technician is injecting foam, it is possible to visually see how foam is migrating through the coils by examining how foam is exiting the back end of the coils. Reference is again made to FIGS. 1-3 for an illustration of foam entering and exiting HVAC coils. Again, it may be possible to visually determine where very deep blockage areas may be located by examining the exit side or back end of the coils. If, for example, foam is being drawn in evenly through the front of the coils but it is not exiting evenly out the back, this will give the technician an idea as to where a deep blockage area is located and can easily work at the target areas until the blockage is removed.

FIGS. 1-3 are screen shots from a coil-cleaning demonstration video that show migration of cleaning foam under low pressure. FIG. 1 illustrates cleaning foam being applied to a front side of the coils. As cleaning foam penetrates through the coils, the foam collects and pulls out particles and debris, effectively removing bacteria and biofilm. FIGS. 2 and 3 illustrate foam exiting the back side of the coils. The process both sterilizes coils and improves air quality. The process furthermore reduces pressure drops, increases air flow and heat transfer, and reduces energy consumption.

In energy savings, improvements may be seen in at least two ways. First, air flow is improved through the system by removing bacteria, biofilm, dirt, grime or other debris. This reduces back pressure, or pressure drop across the coils (differential of pressure before and after the coil). Reducing the pressure drop of an air handler directly reduces the electricity load on the blower that is required to pull air through the coils. In simplistic terms, a 1% reduction in pressure should equate to a 1% reduction in the blower's brake horse power.

In addition to reducing back pressure by removing biofilms and/or other fouling residues from the interior surfaces of the coils, heat transfer by the coils is improved so that air passing through the coils gets colder faster. This helps reduce the energy load of the chilled water chillers. Biofilms reduce cooling capacity by restricting air flow, reducing contact area between moving air and coil surfaces, and providing a layer of organic matter acting as insulation. Removing biofilms increases air flow and contact area between moving air and coil surfaces and mitigates their insulation effect.

An experimental demonstration was performed on an HVAC unit at a luxury hotel in Las Vegas, Nev., which resulted in reductions in both energy load on the blower and cooling capacity by coils. The initial pressure drop across the air handler before cleaning of the heat transfer coils was 0.69 psi. After cleaning the coils using foam according to the invention, the pressure drop across the air handler was reduced to 0.37 psi, which is a 46% reduction. This alone would be expected to lead to about a 46% reduction in the amount of energy required to operate the air handler.

Cooling efficiency was also increased, as indicated by the reduction in the Variable Air Volume (VAV) in various rooms or locations in the hotel. In a VAV system, the volume of air delivered to a room can be increased or decreased by opening and closing of baffles to provide the proper level of cooling. Before cleaning of the coils, the VAVs in a number of rooms were open all the way, or at 100% of air volume capacity. All rooms demanded maximum cooling before cleaning, which was an indication of low cooling efficiency and the inability of the HVAC system to adequately cool all the rooms. After cleaning the coils using foam according to the invention the VAVs in most rooms were reduced by 80-90%. This means that cooling efficiency increased significantly for these areas. The exception was the café kitchen bar, which is constantly being warmed by stoves and ovens and requires constant maximum cooling. By restricting chilled air to rooms that were adequately cooled, more chilled air was available that could be diverted to areas requiring more cooling, such as the kitchen area, thereby more efficiently cooling previously undercooled areas.

Finally, the total water usage for the HVAC cleaning project was 33 gallons, which is approximately 95% less than conventional pressure washing methods. For example, a standard pressure washer may use about 6 gallons per minute during normal operation, which equates to 1,440 gallons of water for 4 hours or cleaning.

The ability of the disclosed methods and systems to deliver a high degree of surface area coverage with cleaning foam makes it possible to sanitize and disinfect coils so as to mitigate antibiotic resistant microbes, such as staph and MRSA in hospitals. Cleaning hospital HVAC coils will reduce energy consumption, and, more importantly, the process will make it finally possible to sanitize and disinfect coils that currently spread disease and infection through the ventilation system. It is the coils and their air handler system that makes it possible for microbes to recirculate and travel throughout a medical facility. By being able to now penetrate through and clean and disinfect the coils, a huge improvement in hospital air quality and health can be achieved. The foam may optionally be used to deliver disinfectant and/or non-stick coatings onto the surface of coils that, when deposited, can inhibit future bacteria from growing.

It should be understood that the inventive methods can be carried out using a variety of different cleaning foams. In some embodiments, a foam generating system for producing cleaning foam used in cleaning a heating, ventilation and air conditioning (HVAC) system of a building comprises: (1) an air pump or pressurized vessel that provides pressurized air; (2) one or more inlets for receiving water, the pressurized air, and a surfactant; (3) one or more air-driven pumps for pressurizing at least the surfactant, the one or more air-driven pumps being driven by the pressurized air; (4) a manifold for receiving and mixing the pressurized air, water, and surfactant so as to form pressurized cleaning foam; and (5) an outlet in fluid communication with the manifold for discharging the pressurized cleaning foam. The following description of an example foam generating system is given by way of example, not limitation.

Figure 4:
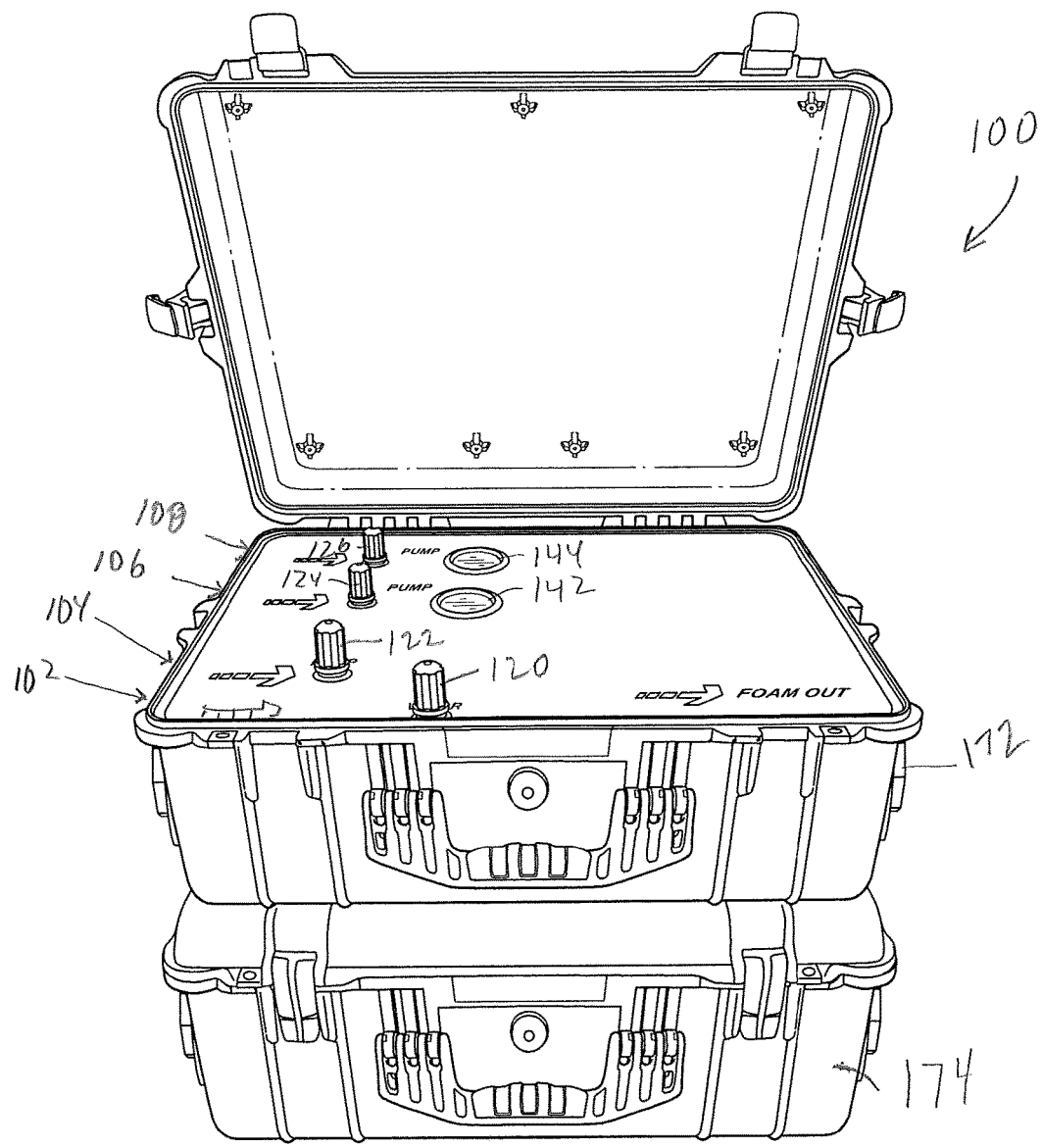
FIG. 4 illustrates an example cleaning foam generating system.
Figure 5:
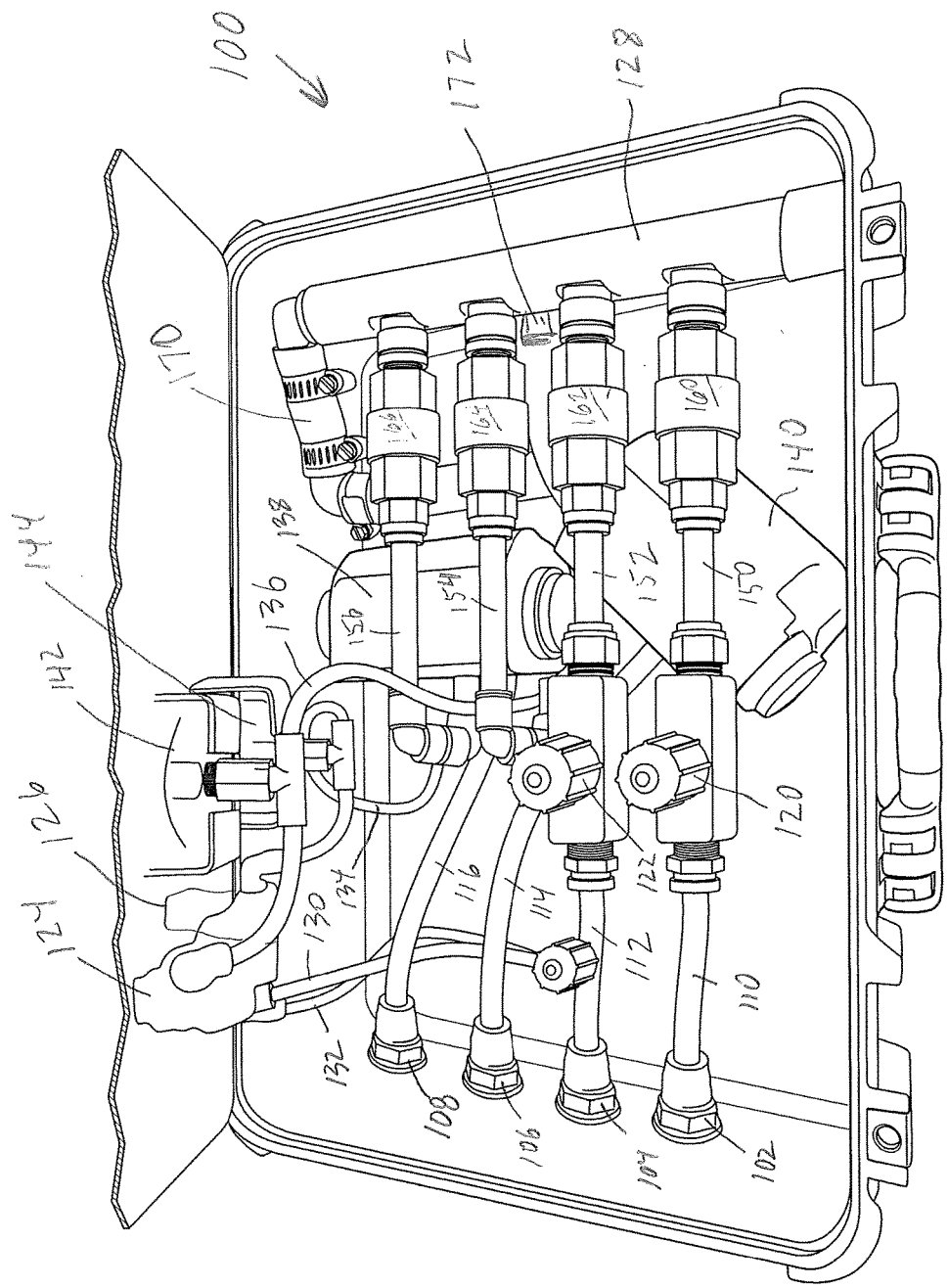
FIG. 5 shows internal components of the portable cleaning foam generating system of FIG. 4.

As illustrated in FIGS. 4 and 5, an example foam generating system 100 can be a compact, lightweight, portable system for generating varying types and volumes of foam. The system 100 can be powered by compressed air (not shown) and includes a water input port 102, an air input port 104, an enzyme and/or chemical input port 106, and a surfactant input port 108 for inputting air, water, enzymes and/or chemical(s), and surfactant, respectively, system 110. Each of input transport lines 110, 112, 114 and 116 are in fluid communication with input ports 102, 104, 106 and 108, respectively, and transport water, air, enzymes and/or chemical(s), and surfactant into system 100 for further processing.

A water valve 120, an air valve 122, a first needle valve 124, and a second needle valve 126 control the flow of input components into system 100. Altering the ratio of input components yields different types of cleaning foam, such as thicker foam, thinner foam, richer foam, diluted foam, adherent foam, runny foam, and the like. Water valve 120 controls the flow and pressure of water delivered to a manifold 128, which serves as a mixing chamber where the components are mixed to make the cleaning foam. Air valve 122 controls the flow and pressure of air into manifold 128. First needle valve 124 controls the flow and pressure of enzymes and/or chemical(s) into manifold 128, and second needle valve 126 controls the flow and pressure of surfactant into manifold 128. By controlling valves 120, 122, 124 and 126, one can adjust the attributes of the cleaning of foam, such as desired consistency, chemistry, volume, pressure, and the like.

While air and water can be introduced into system 100 under pressure to begin with, enzymes, chemical(s) and/or surfactant can be drawn from one or more unpressurized vessels by a pump and pressurized to a desired pressure and flow rate. This can be accomplished using one or more air powered pumps inside system 100.

As shown in FIG. 5, each of first and second auxiliary air lines 130, 132 deliver pressurized air to respective first and second needle valves 124, 126. First and second air pump delivery lines 134, 136 deliver pressurized air from each of first and second needle valves 124, 126, respectively, to each of respective first and second air diaphragm pumps 138, 140. First air diaphragm pump 138 applies pressure to a liquid or solution containing enzymes and/or chemical(s) for introduction under pressure into manifold 128. Second air diaphragm pump 140 applies pressure to a liquid or solution containing surfactant for introduction under pressure into manifold 128. Also provided are first and second pressure gauges 142, 144, which are in fluid communication with respective first and second needle valves 124, 126 and indicate the magnitude of air pressure delivered to each of respective first and second air diaphragm pumps 138, 140. Controlling air pressure to the pumps controls the rate at which first and second air diaphragm pumps 138, 140 pump their respective components to diaphragm 128. Increasing the air pressure increases the rate of pumping, and lowering the air pressure reduces the rate of pumping (e.g., 10 psi for a flow rate of 0.5 gallons per minute (GPM), 20 psi for a flow rate of 0.74 GPM).

Also provided are delivery lines 150, 152, 154 and 156, which are used to deliver, respectively, water, air, enzymes and/or chemical(s) and surfactant to manifold 128. Also provided are check values 160, 162, 164 and 166 along respective delivery lines 150, 152, 154 and 156, which provide for 1-way flow of input components into manifold 128 and prevent components and/or foam from backing up through delivery lines 150, 152, 154 and 156. Foam generated in manifold 128 by mixing of the components under pressure is passed through foam delivery line 170 and out foam outlet 172. Hoses and other equipment (not shown) can be carried in secondary container 174 and attached to system 100 during use. A foam delivery hose and nozzle (not shown) can be used to spray or inject cleaning foam to heat-transfer coils of an HVAC system.

A desired feature of the apparatus and method is the ability to generate different types of foam, such as very thick, very thin, and in-between foam consistencies. Returning to FIGS. 4 and 5, surfactant input port 108 is typically used to draw in surfactant and, in the illustrated embodiment, can be connected to a ½ inch outer diameter (OD) tubing (not shown), which in turn can be connected to a supply of surfactant, such as a pale, bucket, or drum (not shown). Input port 106 is typically used to draw in active chemistry that is desired for cleaning, sanitizing, and disinfecting the coils and can be connected to a ½ inch OD tubing (not shown), which in turn can be connected to a pale, bucket, or drum containing the desired cleaning solution. Also, the surfactant and cleaning solution can alternatively be pre-mixed together in the supply source (pale, bucket, drum) and drawn into either of input ports 106 or 108 by a respective pump 138 or 140. This can be done, for example, where there is no readily available pressurized water supply available at the work site and one of pumps 138 or 140 is needed to draw in water, in place of a water hose supplying pressurized water directly connected to input port 102.

As illustrated, both of input ports 106 and 108 are connected to respective 1-100 psi pressure gauges 142, 144. Each pressure gauge 142, 144 is connected to a respective needle valve 124, 126 and a respective air diaphragm pump 138, 140 and assist the technician visually determine how much air pressure is being applied to each isolated air diaphragm pump 138, 140.

As illustrated, through written instructions printed on a front control panel of system 100, a technician can quickly and easily determine and control the flow rate of liquid through each port via how much pressure is being introduced. By way of illustration, keeping in mind that the system can be adjusted to provide different flow rates at selected air pressures, 10 psi of air pressure can produce a flow rate of 0.50 gallons per minute (GPM) and 20 psi of air pressure can produce a flow rate of 0.74 GPM. This setup allows the technician to adjust the foam generating process to very precise settings so that the volume and percentages of mixing ratios can quickly and easily be determined, providing the ability to make specified cleaning foams containing exact volumes of cleaning solution and surfactant ratios. Once air input port 102 is connected to a pressurized air supply, which can be supplied via a facility internal air supply or via portable air compressors, and the other desired components are available, system 100 is ready for operation.

Air valve 122, which can also be a needle valve, controls the flow of air into manifold 128, which can be the primary mixing chamber. The flow rates of other components through input ports 102, 106 and 108 are controlled by respective valves 120, 124 and 126. Regulation of pressurized air into manifold mixing chamber 128 enables the technician to control the type of foam desired. For example, adding a higher volume of pressurized air into manifold 128 creates a volumized and thick shaving cream-like foam. Foam thickness is also determined by the volume of surfactant and water, which directly affects the ability to generate the type of foam desired. For example, too much water, and too little surfactant will produce a mostly aerosolized type of product. Too much surfactant and too little water will produce an extremely thick foam.

Water input port 102 provides for an external water connection, which may include a garden hose style connection. There may be no internal pump connected to port 102 so water flow is dependent upon external pressure, such as one would find when connected to a garden hose connection. The pressure and volume of water entering port 102 can be regulated by water valve 120, which can be a needle valve, which enables the technician to add or subtract water to further help create the type of foam desired.

Manifold 128 is connected via foam delivery line 170, which can be ¾" OD tubing, to foam outlet port 172. Outlet port 172 may be configured for connecting a hose line (not shown) via a hose barb, cam lock connection, or other hose connecting device. The external hose can be any desired length, such as 25 feet; however, this can be longer depending on application needs. Depending on the volume needs of the project, a technician can connect any size hosing to outlet port 172, such as 1 inch, ¾ inch, ½ inch, etc. Typically, a ½ inch hose connection can be used for cleaning HVAC systems. In some embodiments, there is no need for tips, points, or other special connections attached at the end of the external foam line. Restrictive tips or connections would not necessarily be applied because it may inhibit flow of foam and even operation of the system's air diaphragm pumps. In addition, a key to eliminating the risk of damage to the coils involves not restricting flow at the exiting end of the foam line. When foam exits the foam line and is applied to the coils, the dispersion of energy by a larger opening can be advantageous to the application of foam and eliminate pressurized points of contact which can potentially damage very delicate coils.

Furthermore, although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:
1. A method for cleaning a heating, ventilation and air conditioning (HVAC) system of a building, comprising:
applying a cleaning foam at low pressure into a plurality of spaces between or within one or more heat-transfer coils of a heat exchange system of the HVAC system, the heat exchange system having a front side for air intake during operation of the HVAC system and a back side through which air exits during the operation of the HVAC system, wherein the cleaning foam is applied to the front side of the heat exchange system, wherein the cleaning foam comprises water, air, surfactant, enzymes, and least one of chlorine dioxide, halide salt, hypochlorite salt, organic solvent, quaternary ammonium compound, acid, base, or chelating agent;
causing or allowing the cleaning foam to pass through the plurality of spaces;
the cleaning foam breaking down and removing dirt or debris from surfaces adjacent to the plurality of spaces, including killing and/or removing at least one of bacteria, viruses, fungi, or biofilm from the surfaces, the enzymes assisting in breaking down biofilm if present; and
the cleaning foam carrying away the removed dirt or debris from the plurality of spaces and exiting the back side of the heat exchange system with the removed debris.

2. A method for cleaning and disinfecting a heating, ventilation and air conditioning (HVAC) system of a building, comprising:
- applying a cleaning foam comprising water, air, surfactant, and enzymes into a plurality of spaces between or within one or more heat-transfer coils of a heat exchange system of the HVAC system, the heat exchange system having a front side for air intake during operation of the HVAC system and a back side through which air exits during the operation of the HVAC system, the heat exchange system containing biofilm and dirt or debris, wherein the cleaning foam is applied to the front side of the heat exchange system;
- operating an air handler of the HVAC system, the air handler causing forced air to enter the front side of the heat exchange system and pass through the plurality of spaces and assist movement of the cleaning foam through the plurality of spaces;
- the cleaning foam breaking down and removing the biofilm and the dirt or debris from surfaces adjacent to the plurality of spaces; and
- the cleaning foam carrying away the removed biofilm and the dirt or debris from the plurality of spaces and exiting the back side of the heat exchange system with the removed debris.

3. The method of claim 2, wherein the cleaning foam further comprises at least one of hydrogen peroxide, chlorine dioxide, halide salt, hypochlorite salt, organic solvent, quaternary ammonium compound, acid, base, or chelating agent.

4. A method for cleaning a heating, ventilation and air conditioning (HVAC) system of a building, comprising:
- applying a cleaning foam containing enzymes that break down biofilm into a plurality of spaces between or within one or more heat-transfer coils of a heat exchange system of the HVAC system, the heat exchange system having a front side for air intake during operation of the HVAC system and a back side through which air exits during the operation of the HVAC system, wherein the cleaning foam is applied to the front side of the heat exchange system; during operation of the HVAC system,
- causing or allowing the cleaning foam to pass through the plurality of spaces;
- the cleaning foam breaking down and removing dirt or debris from surfaces adjacent to the plurality of spaces, the enzymes assisting in breaking down biofilm if present; and
- the cleaning foam carrying away the removed dirt or debris, and biofilm if present, from the plurality of spaces and exiting the back side of the heat exchange system with the removed debris.

5. The method of claim 4, wherein the cleaning foam breaks down and removes biofilm from the surfaces and dirt associated with the biofilm.

6. The method of claim 4, wherein the cleaning foam kills and/or removes at least one of bacteria, viruses or fungi from the surfaces.

7. The method of claim 4, wherein the cleaning foam is injected under sufficiently low pressure so that the heat-transfer coils are not damaged and bendable heat-transfer fins of the coils are not damaged.

8. The method of claim 4, wherein the cleaning foam is produced on-sight by a foam generating system, the foam generating system including one or more inlets for receiving water, air and a surfactant, a foam-generating mechanism, an outlet for generated cleaning foam, and a hose or conduit for conducting the generated cleaning foam to the one or more heat-transfer coils.

9. The method of claim 4, further comprising introducing air from at least one of an external air supply, external fan, pressurized air line, or portable blower into the plurality of spaces to assist movement of the cleaning foam and removed debris through at least some of the plurality of spaces.

10. The method of claim 4, the method comprising:
- initially applying a thicker cleaning foam to the plurality of spaces to increase residence time and contact of the cleaning foam to the surfaces; and
- thereafter applying a thinner cleaning foam to the plurality of spaces to accelerate movement of the cleaning foam and removed debris through the plurality of spaces.

11. The method of claim 4, wherein following cleaning of the HVAC system, the HVAC system operates with reduced energy consumption and improved air flow.

12. The method of claim 4, further comprising:
- identifying one or more blockage areas within the one or more coils of the HVAC system; and
- applying additional cleaning foam to the one or more blockage areas.

13. The method of claim 4, wherein the cleaning foam comprises water, air, and surfactant.

14. The method of claim 13, wherein the cleaning foam is free of volatile organic compounds (VOCs) and/or is pH neutral.

15. The method of claim 13, wherein the cleaning foam further comprises at least one of hydrogen peroxide, chlorine dioxide, halide salt, hypochlorite salt, organic solvent, quaternary ammonium compound, acid, base, or chelating agent.

16. The method of claim 4, further comprising operating an air handler of the HVAC system, the air handler causing forced air to pass through the plurality of spaces between or within one or more heat-transfer coils, the forced air assisting movement of the cleaning foam and removed debris through the plurality of spaces.

17. The method of claim 16, the air handler comprising a blower that applies air pressure to a side of the coils and pushes air through the plurality of spaces.

18. The method of claim 16, the air handler comprising a blower that reduces air pressure to a side of the coils and pulls air through the plurality of spaces.

* * * * *

UNITED STATES PATENT AND TRADEMARK OFFICE
CERTIFICATE OF CORRECTION

PATENT NO. : 10,480,875 B2
APPLICATION NO. : 15/280693
DATED : November 19, 2019
INVENTOR(S) : James Metropoulos It is certified that error appears in the above-identified patent and that said Letters Patent is hereby corrected as shown below:

In the Specification

Column 1
Line 9, change "2016" to –2015–

Column 3
Line 4, change "handle held" to –hand-held–

Column 5
Line 48, change "removable" to –removal–

Column 6
Line 2, remove [the]

Column 7
Line 2, change "regards" to –regard–

Column 8
Line 43, change "drop" to –drop,–

Column 11
Line 28, change "technician visually" to –technician to visually–

Signed and Sealed this
Fourth Day of February, 2020

Andrei Iancu
*Director of the United States Patent and Trademark Office*